(12) United States Patent
Harald

(10) Patent No.: US 12,329,353 B2
(45) Date of Patent: Jun. 17, 2025

(54) ENDOSCOPE CHANNEL INFORMATION PROCESSING DEVICE, ENDOSCOPE CHANNEL INSPECTION SYSTEM, AND ENDOSCOPE CHANNEL INFORMATION PROCESSING METHOD

(71) Applicant: HOYA CORPORATION, Tokyo (JP)

(72) Inventor: Huber Harald, Augsburg (DE)

(73) Assignee: HOYA CORPORATION, Tokyo (JP)

( * ) Notice: Subject to any disclaimer, the term of this patent is extended or adjusted under 35 U.S.C. 154(b) by 444 days.

(21) Appl. No.: 17/910,524

(22) PCT Filed: Mar. 12, 2021

(86) PCT No.: PCT/JP2021/009986
§ 371 (c)(1),
(2) Date: Sep. 9, 2022

(87) PCT Pub. No.: WO2021/182600
PCT Pub. Date: Sep. 16, 2021

(65) Prior Publication Data
US 2023/0138418 A1    May 4, 2023

Related U.S. Application Data

(60) Provisional application No. 62/988,495, filed on Mar. 12, 2020.

(51) Int. Cl.
*A61B 1/00* (2006.01)
*A61B 1/12* (2006.01)

(52) U.S. Cl.
CPC ...... *A61B 1/00057* (2013.01); *A61B 1/00009* (2013.01); *A61B 1/00052* (2013.01); *A61B 1/121* (2013.01)

(58) Field of Classification Search
None
See application file for complete search history.

(56) References Cited

U.S. PATENT DOCUMENTS

| 2014/0150782 A1* | 6/2014 | Vazales | A61M 25/1018 128/202.16 |
| 2017/0258550 A1* | 9/2017 | Vazales | A61B 90/70 |

(Continued)

FOREIGN PATENT DOCUMENTS

| JP | 2006-250943 A | 9/2006 |
| JP | 2007-147506 A | 6/2007 |

(Continued)

OTHER PUBLICATIONS

International Search Report issued in International Patent Application No. PCT/JP2021/009986, dated May 25, 2021, along with an English translation thereof.

(Continued)

*Primary Examiner* — John P Leubecker
(74) *Attorney, Agent, or Firm* — GREENBLUM & BERNSTEIN, P.L.C.

(57) ABSTRACT

To provide an information processing device or the like capable of finding channel abnormality early. An information processing device includes: an inspection image acquisition unit configured to acquire an inspection image captured by an inspection endoscope inserted into a channel of an inspection target endoscope; a determination acquisition unit configured to input the inspection image acquired by the inspection image acquisition unit to a model that outputs a determination prediction regarding a state of the channel when the inspection image is input, and to acquire the determination prediction to be output; and an output unit configured to output the inspection image and the determination prediction in association.

10 Claims, 14 Drawing Sheets

(56) References Cited

U.S. PATENT DOCUMENTS

2017/0323163 A1* 11/2017 Leung .................. G06T 3/4046
2018/0067051 A1   3/2018 Baribeau
2018/0084162 A1   3/2018 Stephenson
2019/0224357 A1   7/2019 Sundet et al.
2019/0269468 A1*  9/2019 Hsu ....................... A61B 34/20
2020/0405134 A1* 12/2020 Hameed ............. A61B 1/00029

FOREIGN PATENT DOCUMENTS

| JP | 2012-13675 A | 1/2012 |
| WO | 2019/102679 A | 5/2019 |
| WO | 2019/219955 A1 | 11/2019 |
| WO | 2020/096891 A1 | 5/2020 |

OTHER PUBLICATIONS

European Search Report issued in European application No. 21767767.3, dated Mar. 15, 2024.
Japanese Notice of Reasons for Refusal dated Apr. 18, 2023 issued in family member Japanese Application No. 2022-507296, together with an English translation.
Kavel Visrodia, MD and Bret T. Petersen, MD, "Borescope examination: Is there value in visual assessment of endoscope channels?", Gastrointestinal Endoscopy, 2018, vol. 88, No. 4, p. 620-623.
Office Action issued in Chinese application No. 202180019513.5, dated Oct. 24, 2024.

\* cited by examiner

| S/N | SN1234 |
|---|---|
| DATE AND TIME | 2021/3/1 10:40 |

| POSITION | DETERMINATION RESULT | INSPECTION IMAGE |
|---|---|---|
| 50 | SHALLOW SCRATCH | ***.bmp |
| 62 | SHALLOW SCRATCH | ***.bmp |
| 80 | SLIGHT CONTAMINATION | ***.bmp |

ENDOSCOPE CHANNEL INFORMATION PROCESSING DEVICE, ENDOSCOPE CHANNEL INSPECTION SYSTEM, AND ENDOSCOPE CHANNEL INFORMATION PROCESSING METHOD

TECHNICAL FIELD

The present invention relates to an information processing device, an inspection system, a program, and an information processing method.

BACKGROUND ART

An endoscope that has a channel through which a treatment tool can be inserted is used for examination and medical treatment of a hollow organ such as an alimentary tract (see Cited Literature 1).

CITATION LIST

Patent Literature

Patent Literature 1: WO 2019/102679 A

SUMMARY OF INVENTION

Technical Problem

When a hole is made in a channel of an endoscope and water, contaminant, or the like enters the inside of the endoscope, it is necessary to replace most of the components of the endoscope. Therefore, an expensive repairing cost is required.

An objective of an aspect is to provide an information processing device or the like that can find an abnormality of a channel early.

Solution to Problem

An information processing device includes: an inspection image acquisition unit configured to acquire an inspection image captured by an inspection endoscope inserted into a channel of an inspection target endoscope; a determination acquisition unit configured to input the inspection image acquired by the inspection image acquisition unit to a model that outputs a determination prediction regarding a state of the channel when the inspection image is input, and to acquire the determination prediction to be output; and an output unit configured to output the inspection image and the determination prediction in association.

Advantageous Effects of Invention

In one aspect, it is possible to provide an information processing device or the like that can find an abnormality of a channel early.

DESCRIPTION OF EMBODIMENTS

First Embodiment

Figure 1:
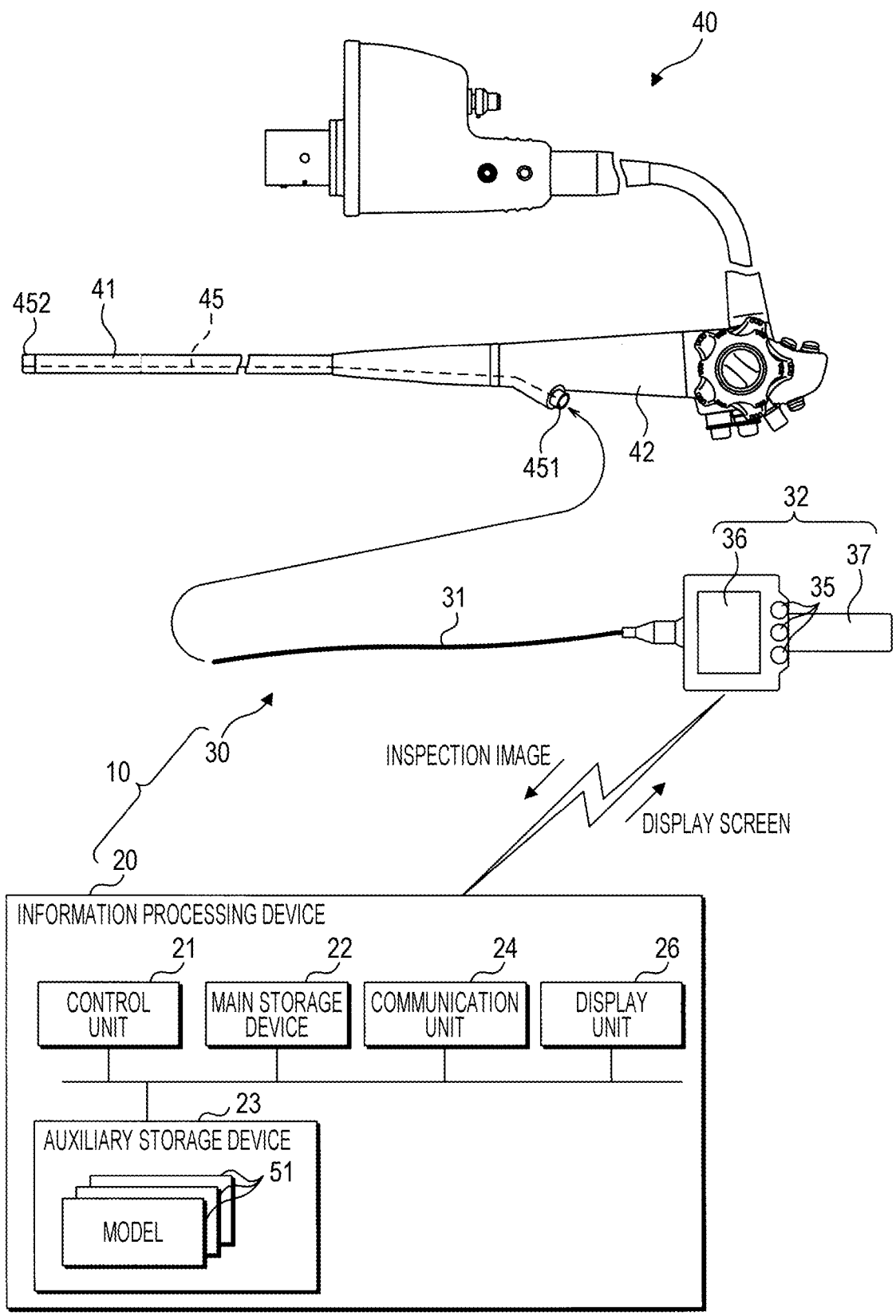
FIG. 1 is an explanatory diagram illustrating a configuration of an inspection system.

FIG. 1 is an explanatory diagram illustrating a configuration of an inspection system 10. The inspection system 10 is used to inspect an inspection target endoscope 40 that has been cleaned and disinfected after being used for endoscopic examination. The inspection system 10 includes an information processing device 20 and an inspection endoscope 30.

The information processing device 20 includes a control unit 21, a main storage device 22, an auxiliary storage device 23, a communication unit 24, a display unit 26, and a bus. The control unit 21 is an arithmetic control device that executes a program according to the present embodiment. In the control unit 21, one or a plurality of central processing units (CPUs), graphics processing units (GPUs), multi-core CPUs, or the like is used. The control unit 21 is connected to each hardware unit included in the information processing device 20 via the bus.

The main storage device 22 is a storage device such as a static random access memory (SRAM), a dynamic random access memory (DRAM), or a flash memory. The main storage device 22 temporarily stores information required during processing performed by the control unit 21 and a program which is being executed by the control unit 21.

The auxiliary storage device 23 is a storage device such as an SRAM, a flash memory, a hard disk, or a magnetic tape. The auxiliary storage device 23 stores a plurality of models 51, a program to be executed by the control unit 21, and various kinds of data necessary for executing the program. The communication unit 24 is an interface that performs communication between the information processing device 20 and the inspection endoscope 30 and communication between the information processing device 20 and a hospital information system (HIS) (not illustrated).

The display unit 26 is, for example, a liquid crystal display or an organic electroluminescence (EL) display.

The information processing device 20 is a general-purpose personal computer, a tablet, a smartphone, a large computer, a virtual machine running on a large computer, a cloud computing system, or a quantum computer. The information processing device 20 may be a plurality of personal computers or the like that performs distributed processing. The information processing device 20 may be embedded in the inspection endoscope 30. In such a case, a communication function between the information processing device 20 and the inspection endoscope 30 is unnecessary.

The inspection endoscope 30 includes an insertion portion 31 and an operation unit 32. The operation unit 32 includes a display unit 36, an operation button 35, and a grip portion 37. The display unit 36 is, for example, a liquid crystal display or an organic EL display.

The inspection endoscope 30 is, for example, a so-called video endoscope that includes a light emitting element and an image sensor at the distal end of the insertion portion 31. The inspection endoscope 30 may include an imaging fiber and an illumination fiber inside the insertion portion 31 and may capture an image transmitted through the imaging fiber using an image sensor provided inside the operation unit 32. The image sensor implements a function of the imaging unit according to the present embodiment.

The operation button 35 is allocated to functions such as an operation of turning on or off power, an operation of a cursor displayed on the display unit 36, starting and ending of recording of a moving image, recording of a still image, and selection of an image to be displayed on the display unit 36. The functions allocated to each operation button 35 may be able to be appropriately set by the user. The inspection endoscope 30 may receive an operation from the user via a voice input, wireless communication, or the like instead of the operation button 35.

The inspection endoscope 30 includes a communication unit (not illustrated) and sequentially transmits images captured by the image sensor to the information processing device 20. The communication unit implements the function of an inspection image output unit according to the present embodiment.

The inspection endoscope 30 displays a display screen received from the information processing device 20 on the display unit 36. The inspection endoscope 30 is, for example, a general-purpose industrial endoscope that has a wireless communication function. The inspection endoscope 30 may be dedicated to the inspection system 10 according to the present embodiment. The control unit 21 may cause the display unit 26 to display an image similar to that of the display unit 36.

The inspection target endoscope 40 is, for example, an upper gastrointestinal tract endoscope. The inspection target endoscope 40 includes an operation unit 42 and an insertion portion 41. A channel 45 disposed inside the insertion portion 41 penetrates from a channel inlet 451 provided in the operation unit 42 to a channel outlet 452 disposed at the distal end of the insertion portion 41.

The insertion portion 31 of the inspection endoscope 30 has a thickness that can be inserted into the channel 45 from the channel inlet 451 and a length that can reach the channel outlet 452. That is, the user uses the inspection endoscope 30 that includes the insertion portion 31 corresponding to the specification of the channel 45 of the inspection target endoscope 40.

Even when the inspection endoscope 30 comes into contact with the inner surface of the channel 45 of the inspection target endoscope 40 on which reprocessing such as cleaning and disinfection has been completed, the inspection endoscope 30 can be cleaned to a level at which reprocessing on the inspection target endoscope 40 does not need to be performed again. That is, the inspection endoscope 30 can perform reprocessing at the same level as that of the inspection target endoscope 40. It is desirable that the inspection endoscope 30 be reprocessed whenever the inspection endoscope 30 is used. Since the inspection endoscope 30 does not include a channel or, an air or water supply duct, cleaning and disinfection can be easily performed as compared with the inspection target endoscope 40. The inspection endoscope 30 may be of a so-called cover type on which a clean cover is put with every use.

After the endoscopic examination ends, the user performs reprocessing such as cleaning and disinfection on the inspection target endoscope 40 in conformity with a predetermined protocol. The user holds the grip portion 37 in one hand and the insertion portion 31 in the opposite hand and inserts the insertion portion 31 into the channel 45 while viewing the display unit 36. An inspection image inside the channel 45 is captured by the inspection endoscope 30. The captured inspection image is displayed on the display unit 36 in real time.

Figure 2:
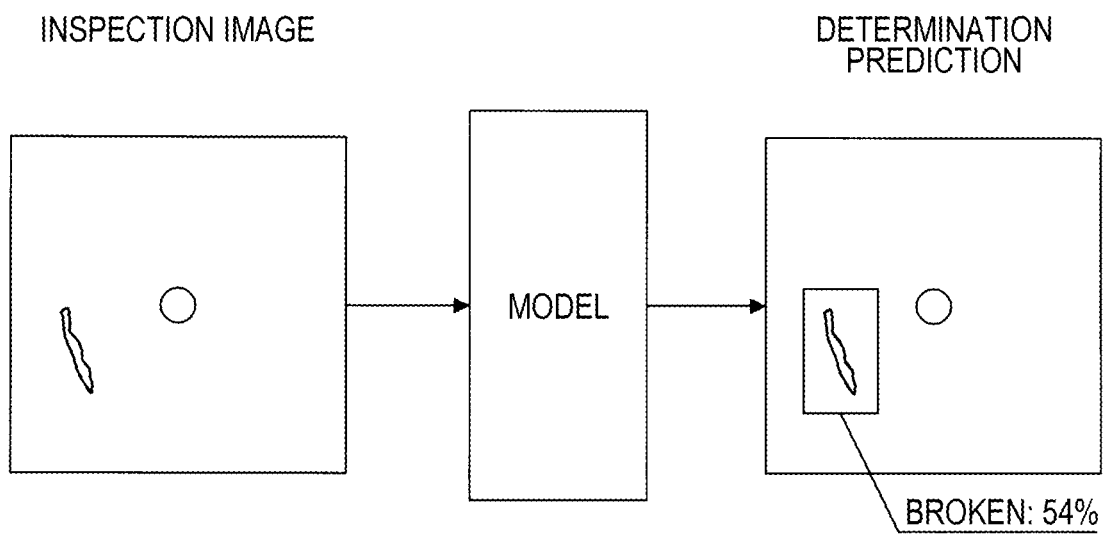
FIG. 2 is an explanatory diagram illustrating a configuration of a model.

FIG. 2 is an explanatory diagram illustrating a configuration of the model 51. The model 51 receives an inspection image captured by the inspection endoscope 30 and outputs a determination prediction regarding an abnormality in the channel 45. In the example illustrated in FIG. 2, the determination prediction indicating with an accuracy of 54% that the channel 45 is likely to be broken is output in the obliquely lower left portion of the inspection image. In the following description, a prediction that has a predetermined accuracy or more is referred to as a "determination result".

The model 51 is generated, for example, by machine learning using a large amount of training data obtained by combining an inspection image and a state of the channel 45 determined when an expert observes the inspection image. The model 51 may be a program or the like that performs image processing on the inspection image and determines the state of the channel 45 on a rule basis.

The model 51 is generated for each feature such as an application of the inspection target endoscope 40 and a specification of the channel 45, and is recorded in the auxiliary storage device 23. The model 51 may be generated for each model type of the inspection target endoscope 40. An example of the model 51 is shown in Table 1. In Table 1, a channel diameter is an inner diameter of the channel 45.

TABLE 1

| No. | Feature of inspection target endoscope |
|---|---|
| 1 | Upper gastrointestinal tract endoscope channel diameter 3.8 mm |
| 2 | Upper gastrointestinal tract endoscope channel diameter 2.8 mm |
| 3 | Upper gastrointestinal tract endoscope channel diameter: 2.0 mm |
| 4 | Duodenum endoscope channel diameter 4.2 mm |
| 5 | Lower gastrointestinal tract endoscope channel diameter 3.8 mm |
| 6 | Lower gastrointestinal tract endoscope channel diameter 3.2 mm |
| 7 | Ultrasonic endoscope channel diameter 4.0 mm |
| 8 | Ultrasonic endoscope channel diameter 2.8 mm |
| 9 | Respiratory endoscope channel diameter 2.8 mm |
| 10 | Respiratory endoscope channel diameter 1.2 mm |

Even in the inspection target endoscope 40 that has the same channel diameter, a state of the channel 45 can be accurately determined by using the model 51 that differs depending on an application. For example, in the ultrasonic endoscopes No. 7 and No. 8, the puncture needle is often inserted into the channel 45. Therefore, the inner surface of the channel 45 is likely to be scratched in the longitudinal direction. The models 51 of No. 7 and No. 8 for which machine learning has been performed using an inspection image of an ultrasonic endoscope are trained so that scratches in the longitudinal direction can be accurately determined.

When there is a plurality of model types of inspection endoscopes 30 that are likely to be used for the inspection target endoscope 40 that has the same features, the model 51 is preferably prepared for each model type of the inspection endoscopes 30. This is because a viewing method of the inner surface of the channel 45 may differ depending on the mode type of inspection endoscope 30.

For the inspection target endoscope 40 that has the same feature, the model 51 may be prepared for each abnormality which is a detection target. For example, the model 51 determining a scratch of the channel 45 and the model 51 determining contamination may be separately prepared. It is possible to provide the inspection system 10 that accurately determines each abnormality.

Figure 3:
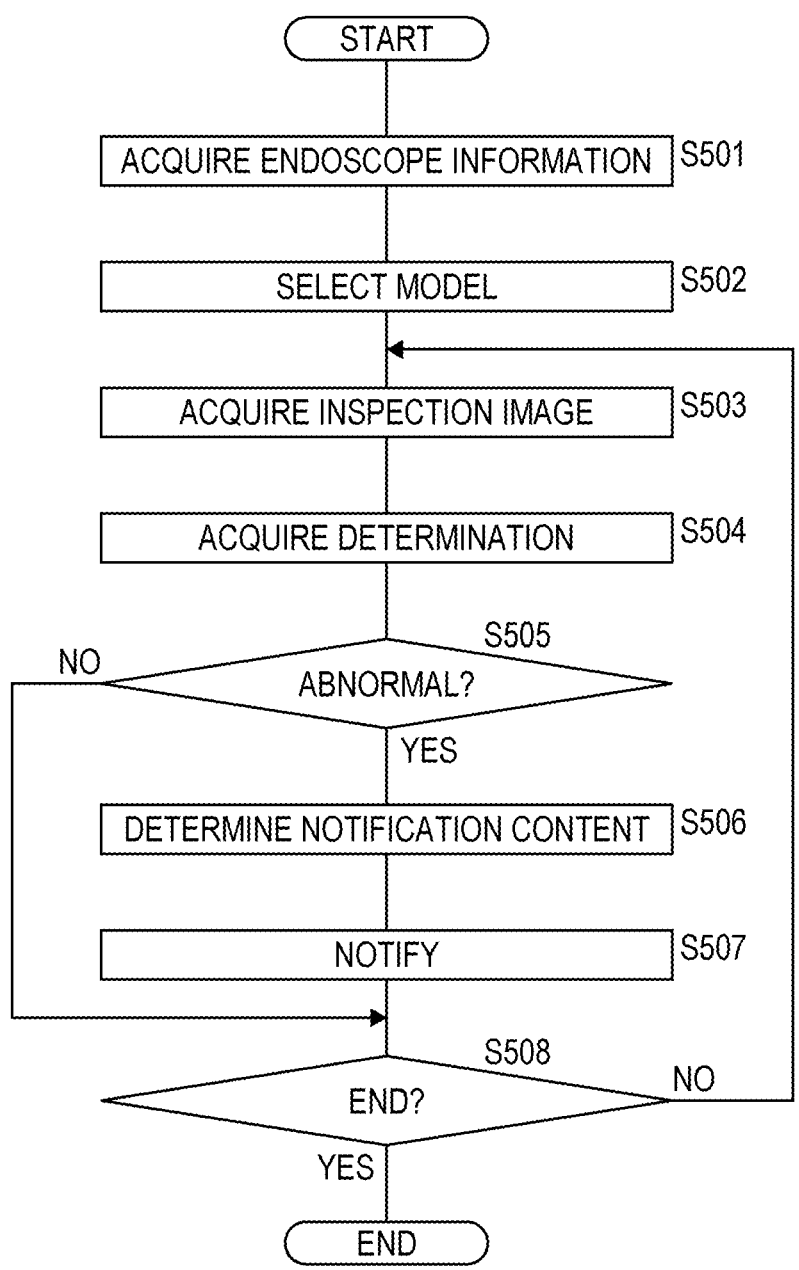
FIG. 3 is a flowchart illustrating a flow of processing of a program.

FIG. 3 is a flowchart illustrating a flow of processing of a program. The control unit 21 acquires information regarding a model type of the inspection target endoscope 40 or the like, that is, endoscope information (step S501). For example, the control unit 21 receives an input of information regarding the inspection target endoscope 40 from the user via a microphone, a keyboard, or the like (not illustrated).

The control unit 21 may read an RFID attached to the inspection target endoscope 40 via an RFID reader (not illustrated) and determine a model type. The control unit 21 may determine a model type by capturing the appearance of the inspection target endoscope 40 or a nameplate attached to the inspection target endoscope 40 with a camera (not illustrated). In step S501, the control unit 21 implements a function of an endoscope information acquisition unit according to the present embodiment.

The control unit 21 selects the model 51 corresponding to the model type of the inspection target endoscope 40 (step S502). In step S502, the control unit 21 realizes the function of the model selection unit of the present embodiment.

The control unit 21 acquires the inspection image transmitted from the inspection endoscope 30 (step S503). The control unit 21 inputs the inspection image acquired in step S503 to the model 51 selected in step S502 and acquires the output determination result (step S504). In step S504, the control unit 21 implements the function of the determination acquisition unit according to the present embodiment.

The control unit 21 determines whether the determination result acquired from the model 51 includes information indicating an abnormality of the channel 45 (step S505). The control unit 21 may determine that information indicating the abnormality is included when accuracy of the abnormality included in the information output from the model 51 exceeds a predetermined threshold.

When it is determined that the information indicating the abnormality is included (YES in step S505), the control unit 21 determines notification contents of which the user is notified (step S506). The notification contents are determined for each determination result by the model 51. Table 2 illustrates an example of a relationship between the determination result and the notification contents.

TABLE 2

| Determination result | Notification content |
| --- | --- |
| Broken | Cannot be used. Channel needs to be replaced or repaired. |
| Medium scratch | At next periodic inspection, channel needs to be replaced or repaired channel. |
| Shallow scratch | There is scratch in channel. Handle treatment tool with care. |
| Severe pollution | Cannot be used. Channel needs to be replaced or repaired. |
| Medium pollution | Contamination remains. Perform reprocessing again. At next periodic inspection, channel needs to be replaced or repaired. |
| Slight pollution | Pollution remains. Perform reprocessing again. |

Table 2 is exemplary, and the abnormality determined by the model 51 is not limited to the items shown in Table 2. The model 51 may determine, for example, buckling of the channel 45, buckling marks indicating buckling once and then returning, deformation, coloration, or the like.

The notification contents of which the user is notified by the control unit 21 are also not limited to the contents shown in Table 2. The control unit 21 may record an inspection image in which an abnormality has been detected in the auxiliary storage device 23. When the user gives an instruction to capture a still image using the operation button 35, the control unit 21 records the still image of the inspection image in the auxiliary storage device 23.

The control unit 21 notifies the user of the notification contents determined in step S506 (step S507). The notification is displayed on, for example, the display unit 36. The notification may be performed by voice output. The notification may be performed by vibrating the operation unit 32 or the grip portion 37. In the following description, a case where the control unit 21 performs notification via the display unit 36 will be described as an example.

When it is determined that the information indicating the abnormality is not included (NO in step S505) or after step S507 ends, the control unit 21 determines whether to end the processing (step S508). For example, when the inspection endoscope 30 is removed from the channel 45, the control unit 21 determines to end the processing. The control unit 21 may determine to end the processing when the user operates the operation button 35 to give an instruction to end the inspection.

When the control unit 21 determines not to end the processing (NO in step S508), the control unit 21 returns to step S503. When the control unit 21 determines to end the processing (YES in step S508), the control unit 21 ends the processing.

Figure 4:
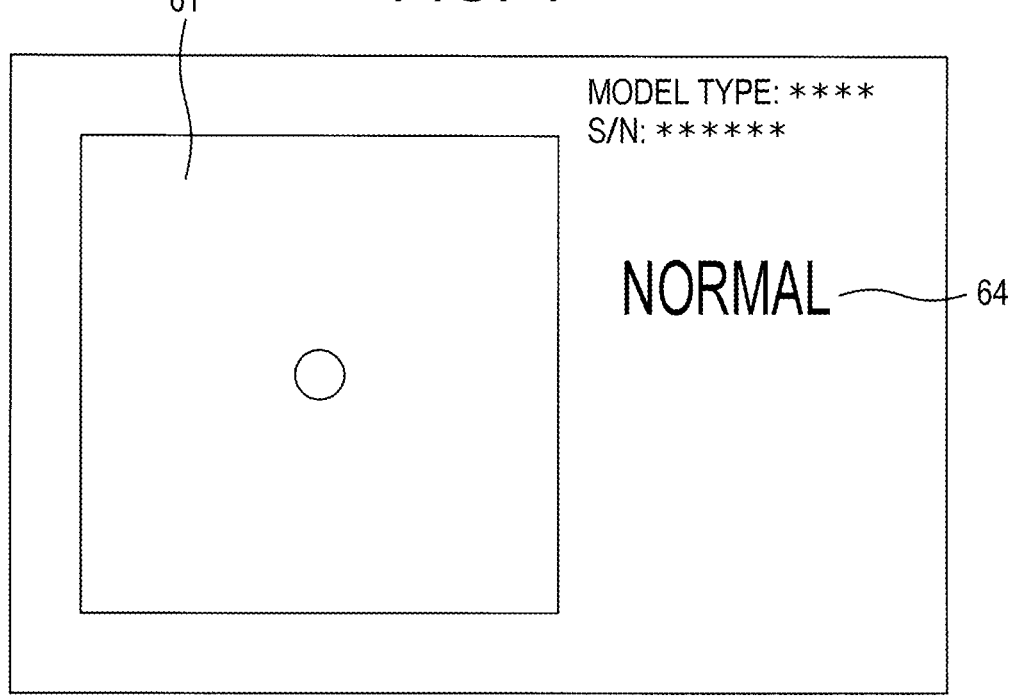
FIG. 4 is an explanatory diagram illustrating an exemplary screen.
Figure 5:
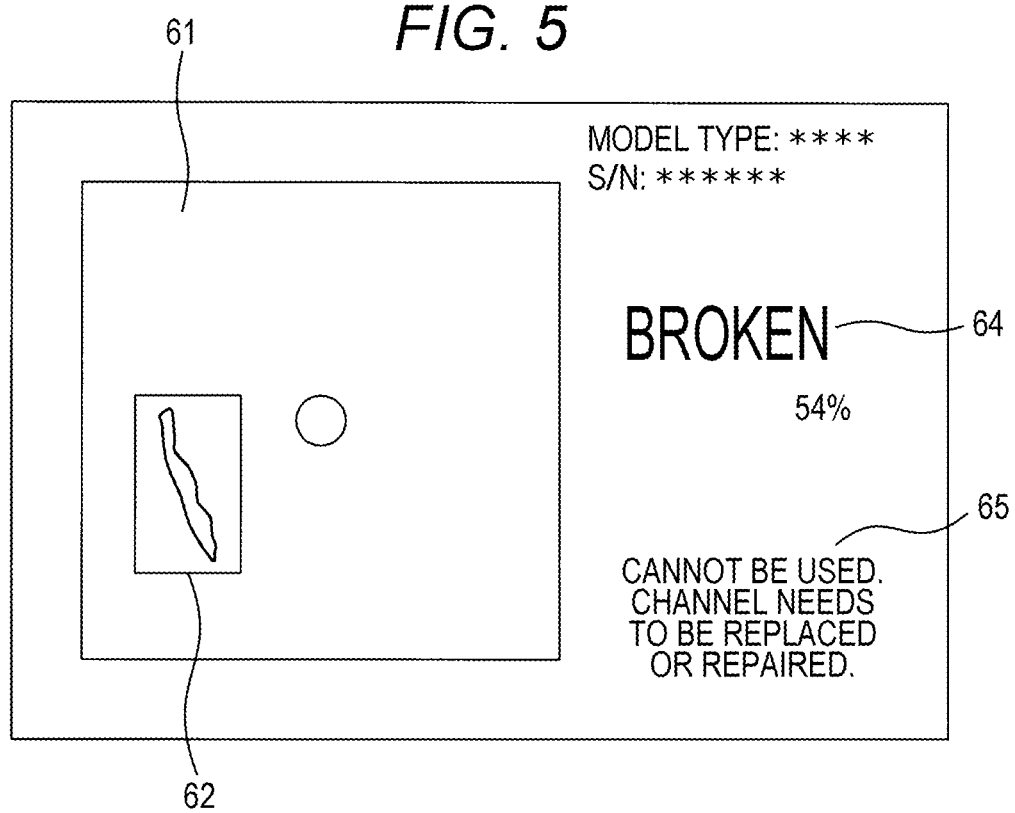
FIG. 5 is an explanatory diagram illustrating an exemplary screen.
Figure 6:
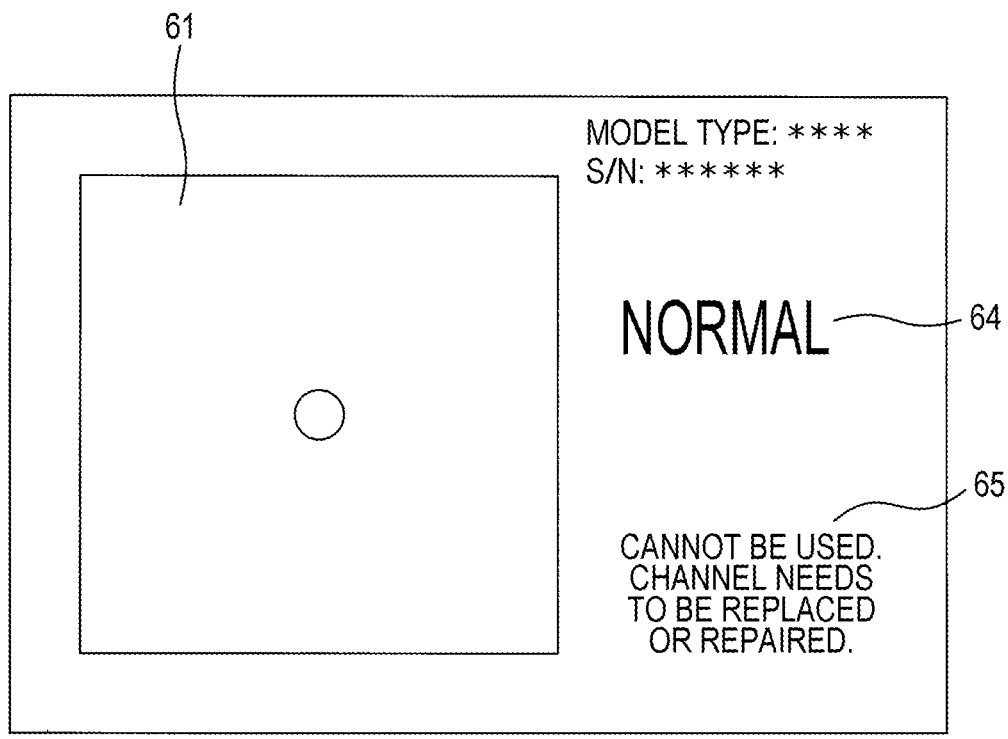
FIG. 6 is an explanatory diagram illustrating an exemplary screen.

FIGS. 4 to 6 are explanatory diagrams illustrating exemplary screens. The control unit 21 displays the screens illustrated in FIGS. 4 to 6 on the display unit 36 via the communication unit 24. With the screens illustrated in FIGS. 4 to 6, control unit 21 implements a function of an output unit according to the present embodiment.

FIG. 4 illustrates an example of a case where an abnormality has not been detected once in the inspection images captured by the inspection endoscope 30. An inspection image field 61, a determination field 64, a model type of the inspection target endoscope 40, and the like are displayed on the screen. In the inspection image field 61, the inspection image is displayed in real time. "Normal" is displayed in the determination field 64.

FIG. 5 illustrates an example of a case where it is determined that the channel 45 is broken based on the inspection image. A notification contents field 65 is added to the screen. An abnormal portion frame 62 indicating a portion where an abnormality is detected is superimposed and displayed on a real-time image displayed in the inspection image field 61. In the determination field 64, a message indicating "broken" is determined and a message indicating that accuracy of the determination is 54% are displayed. The notification contents corresponding to the determination result of "broken" is displayed in the notification contents field 65. The user can confirm that a location which is being observed is broken. Further, the user can confirm that the inspection target endoscope 40 cannot be used and that quick repairing is required.

The control unit 21 may display the accuracy of the determination in accordance with a shape or color of abnormal portion frame 62. For example, the control unit 21 displays the abnormal portion frame 62 with a thin line when the accuracy is low, and displays the abnormal portion frame 62 with a thick line when the accuracy is high. The control unit 21 may display a type of detected abnormality in accordance with the shape or color of the abnormal portion frame 62. For example, the control unit 21 displays the abnormal portion frame 62 indicating a location where breakage has been detected in red, and displays the abnormal portion frame 62 indicating a location where a shallow scratch has been detected in blue.

FIG. 6 illustrates an example of a case where the inspection is continued after the display of FIG. 5 is performed. No abnormality is detected in the real-time inspection image displayed in the inspection image field 61. "Normal" is displayed in the determination field 64. In the notification contents field 65, the notification contents displayed in FIG. 5 are displayed as they are.

When a plurality of abnormalities is detected, the control unit 21 displays notification contents in which there is no overlapping in a state of being listed in the notification contents field 65. In this way, it is possible to prevent the contents to be displayed in the notification contents field 65 from becoming excessive when the user observes the same location a plurality of times by moving the insertion portion 31 back and forth inside the channel 45.

In step S507, the control unit 21 may notify a manufacturer of the inspection target endoscope 40 that an abnormality has been detected. The control unit 21 may transmit the inspection image in which the abnormality has been found along with the notification. The manufacturer collects the inspection target endoscope 40 or advances a periodic inspection time based on the notification. It is possible to provide the inspection system 10 for which a necessary repair is quickly arranged.

According to the present embodiment, it is possible to provide the inspection system 10 in which the user can visually confirm an internal state of the channel 45 using the inspection endoscope 30. According to the present embodiment, by using the model 51, it is possible to provide the inspection system 10 capable of appropriately determining whether the inspection target endoscope 40 can be continuously used even by a user who is unfamiliar with observation of the inside of the channel 45.

According to the present embodiment, it is possible to provide the inspection system 10 that prevents the user from overlooking the abnormality and forgetting to find an abnormality and continuously using the inspection target endoscope 40 by continuously displaying the notification contents field 65 when the abnormality has been detected once.

According to the present embodiment, it is possible to provide the inspection system 10 that prompts the user to perform reprocessing again when sufficient reprocessing cannot be performed in a normal procedure due to a scratch or the like inside the channel 45. For example, the user checks the length of the insertion of the inspection endoscope 30 into the channel 45, and brushes the spot where contamination remains intensively. Thereafter, the user puts the inspection target endoscope 40 in an endoscope cleaning and disinfecting device to perform cleaning and disinfecting.

According to the present embodiment, by using the sufficiently clean inspection endoscope 30, the inspection target endoscope 40 inspected using the inspection endoscope 30 can be used as it is in a next endoscopic examination.

According to the present embodiment, it is possible to provide the inspection system 10 capable of finding an abnormality of the inspection target endoscope 40 at a stage of air supply before the abnormality is found in the leakage test. It is possible to provide the inspection system 10 that reduces maintenance cost of the inspection target endoscope 40 by finding an abnormality early and performing an appropriate repair.

The insertion portion 31 may be inserted into a duct other than the channel 45, such as an air supply duct or a water supply duct of the inspection target endoscope 40. It is possible to provide the inspection system 10 capable of inspecting a duct other than the channel 45.

The inspection target endoscope 40 may be a rigid endoscope such as a laparoscope. The inspection target endoscope 40 may be a non-medical endoscope such as an industrial endoscope.

Second Embodiment

The present embodiment relates to an inspection system 10 that records a location where it is determined that there is an abnormality. Descriptions of portions common to those of the first embodiment will be omitted.

Figures 7, 8:
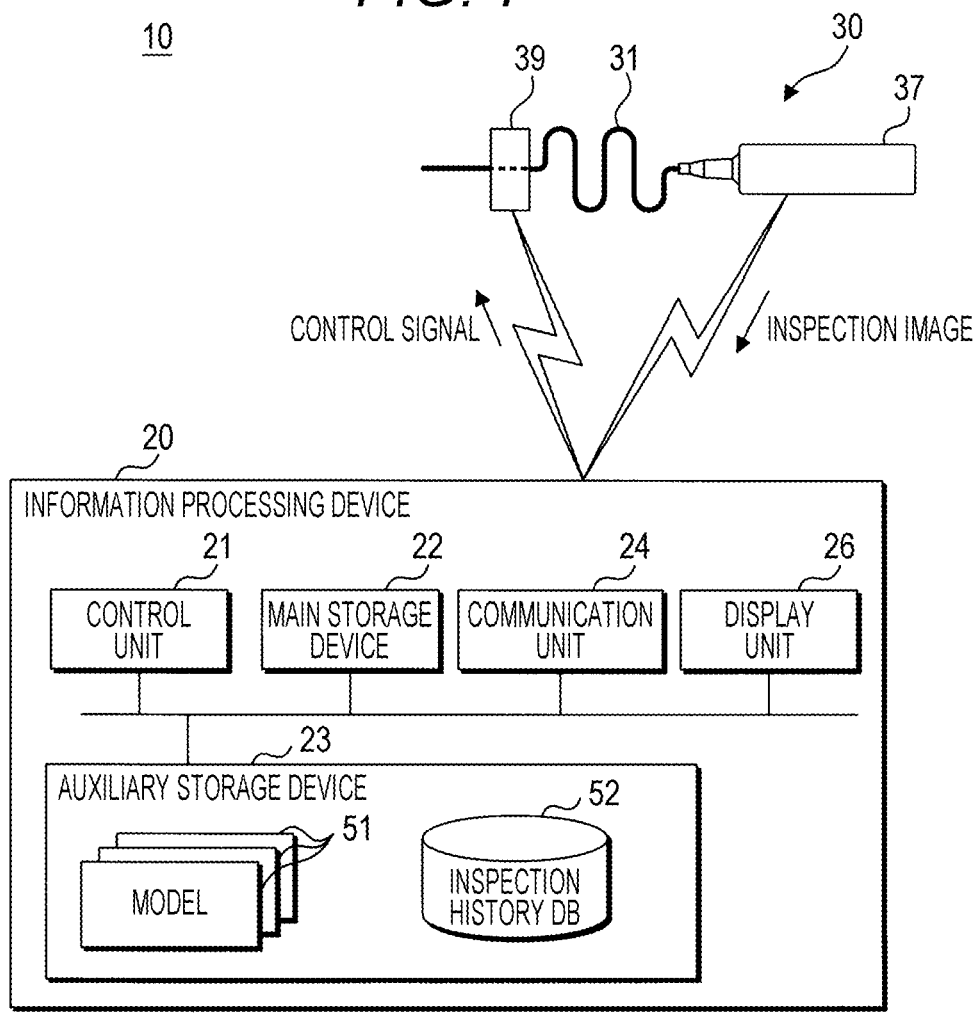
FIG. 7 is an explanatory diagram illustrating a configuration of an inspection system according to a second embodiment.
FIG. 8 is an explanatory diagram illustrating a record layout of an inspection history DB.

FIG. 7 is an explanatory diagram illustrating a configuration of the inspection system 10 according to a second embodiment. The inspection system 10 includes an information processing device 20, an inspection endoscope 30, and an advance and retreat device 39.

The information processing device 20 includes a control unit 21, a main storage device 22, an auxiliary storage device 23, a communication unit 24, a display unit 26, and a bus. In the auxiliary storage device 23, an inspection history DB 52 is recorded in addition to the plurality of models 51, a program to be executed by the control unit 21, and various kinds of data necessary for executing the program. The inspection history DB 52 may be recorded in an external storage device connected to the information processing device 20.

The inspection endoscope 30 includes an insertion portion 31 and a grip portion 37. The inspection endoscope 30 includes a communication unit (not illustrated) and transmits an image captured by the image sensor to the information processing device 20.

The advance and retreat device 39 is an actuator that advances or retreats the insertion portion 31 based on a control signal received from the information processing device 20. The advance and retreat device 39 has a mechanism that advances and retreats the insertion portion 31 while keeping an insertion portion clean, and inserts and removes the insertion portion 31 into and from the channel 45.

FIG. 8 is an explanatory diagram illustrating a record layout of the inspection history DB 52. The inspection history DB 52 includes an S/N field, a date and time field, a position field, a determination result field, and an inspection image field.

In the S/N field, a serial number uniquely assigned to the inspection target endoscope 40 is recorded. In the date and time field, a date and time when the inspection of the inspection target endoscope 40 is started is recorded. In the position field, a position of the distal end of the insertion portion 31 when abnormality is detected in the inspection image is recorded. The position is represented by, for example, a length of the insertion portion 31 inserted from the channel inlet 451.

In the determination result field, the inspection image is input to the model 51 and the output determination result is recorded. In the inspection image field, the inspection image is recorded. In the inspection image field, both an inspection image on which the abnormal portion frame 62 is superimposed and an inspection image on which the abnormal portion frame 62 is not superimposed may be recorded. The inspection history DB 52 has one record for one abnormal point.

Figure 9:
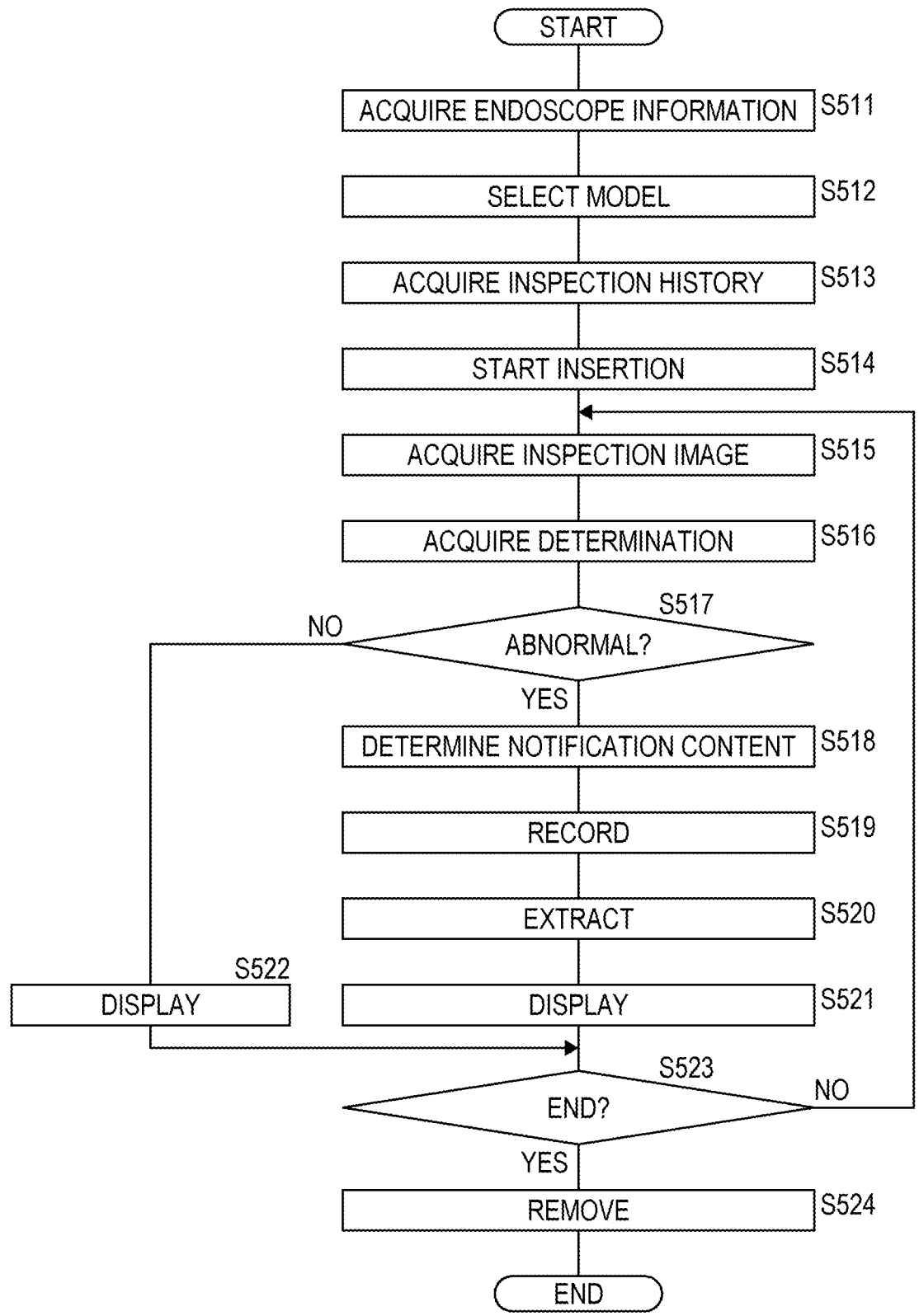
FIG. 9 is a flowchart illustrating a flow of processing of a program according to the second embodiment.

FIG. 9 is a flowchart illustrating a flow of processing of a program according to the second embodiment. The control unit 21 acquires information regarding a model type, a serial number, and the like of the inspection target endoscope 40 (step S511). The control unit 21 selects the model 51 corresponding to the model type of the inspection target endoscope 40 (step S512).

The control unit 21 retrieves the inspection history DB 52 using the serial number acquired in step S511 as a key and acquires a history of the inspection previously performed on the same inspection target endoscope 40 (step S513). The control unit 21 may acquire an inspection history for a predetermined number of times or a predetermined period, for example.

The control unit 21 controls the advance and retreat device 39 such that insertion of the insertion portion 31 into the channel 45 starts (step S514). The advance and retreat device 39 inserts the insertion portion 31 into the channel 45 at a predetermined speed based on an instruction from the control unit 21. The inspection endoscope 30 transmits a captured inspection image to the control unit 21. The control unit 21 may sequentially instruct an amount of insertion to the advance and retreat device 39. The control unit 21 can determine a position at which the inspection image acquired in real time is captured based on an instruction issued to the advance and retreat device 39. The control unit 21 implements a function of the position acquisition unit according to the present embodiment in cooperation with the advance and retreat device 39.

The control unit 21 may detect a marker provided on the surface of the insertion portion 31 from an image acquired from a camera installed near the channel inlet 451 and determine a position at which the inspection image has been captured.

The control unit 21 acquires the inspection image transmitted from the inspection endoscope 30 (step S515). In step S515, the control unit 21 implements a function of an inspection image acquisition unit according to the present embodiment. The control unit 21 inputs the inspection image acquired in step S515 to the model 51 selected in step S512 and acquires the output determination result (step S516).

The control unit 21 determines whether the determination result acquired from the model 51 includes information indicating an abnormality of the channel 45 (step S517).

When it is determined that information indicating the abnormality is included (YES in step S517), the control unit 21 determines notification contents to be notified to the user (step S518).

The control unit 21 generates a new record in the inspection history DB 52 and records the position, the determination result, and the inspection image when the inspection image determined to have the abnormality is captured (step S519). In step S519, the control unit 21 implements a function of an inspection history recording unit according to the present embodiment.

The control unit 21 extracts a past inspection image captured at the same position or a nearby position from the history acquired in step S513 (step S520). In step S520, the control unit 21 implements a function of an extraction unit according to the present embodiment. The control unit 21 displays the real-time inspection image, the determination result, and the extracted past inspection image on the display unit 26 (step S521).

When it is determined that the information indicating the abnormality is not included (NO in step S517), the control unit 21 displays the real-time inspection image and the determination result on the display unit 26 (step S522).

After step S521 or step S522 ends, the control unit 21 determines whether the processing ends (step S523). For example, when the insertion portion 31 reaches the channel outlet 452, the control unit 21 determines to end the processing.

When it is determined that the process does not end (NO in Step S523), the control unit 21 returns to step S515. When it is determined that the process ends (YES in step S523), the control unit 21 controls the advance and retreat device 39 such that the insertion portion 31 is removed from the channel 45 (step S524). In steps S514 and S524, the control unit 21 implements a function of the advance/retract control unit according to the present embodiment. After that, the control unit 21 ends the processing.

Figure 10:
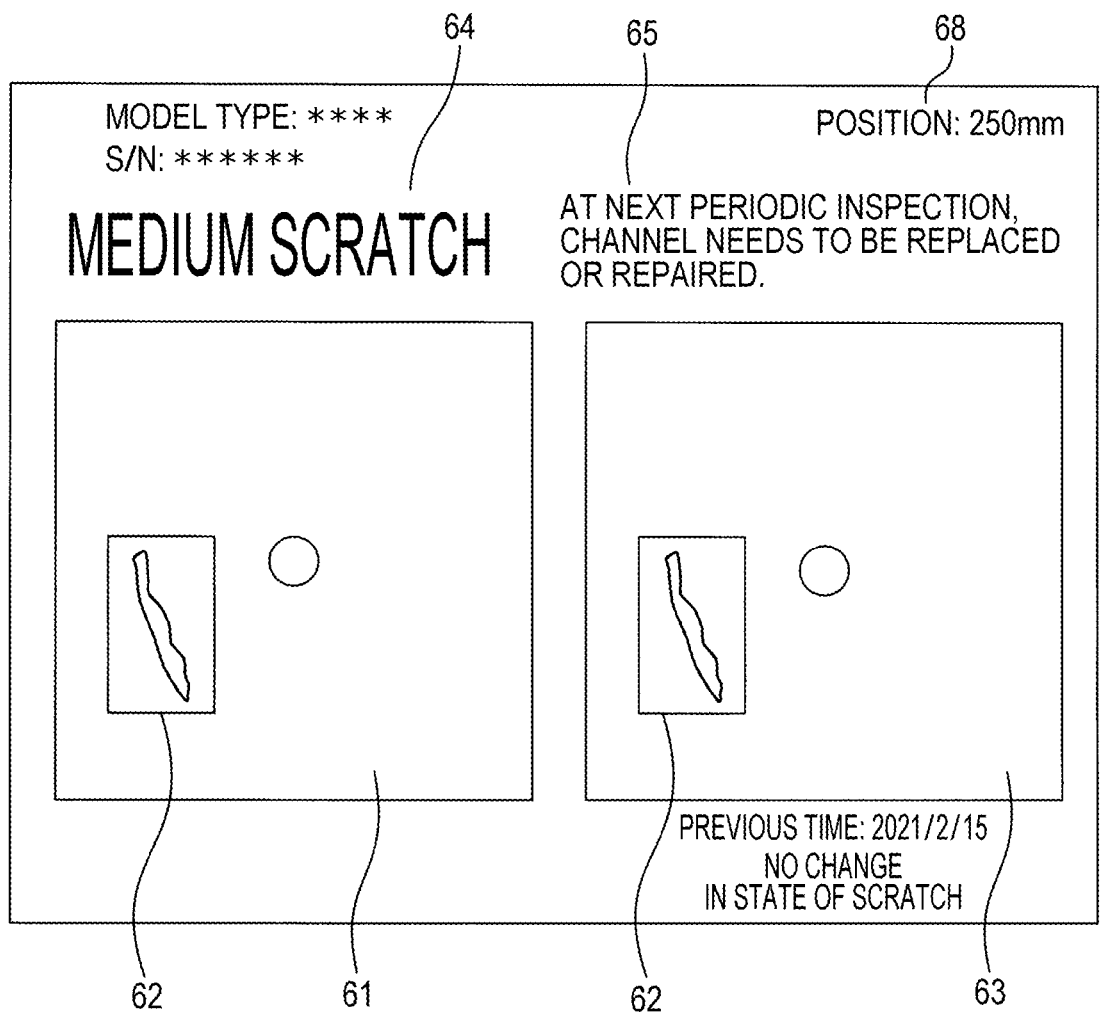
FIG. 10 is an explanatory diagram illustrating an exemplary screen according to the second embodiment.
Figure 11:
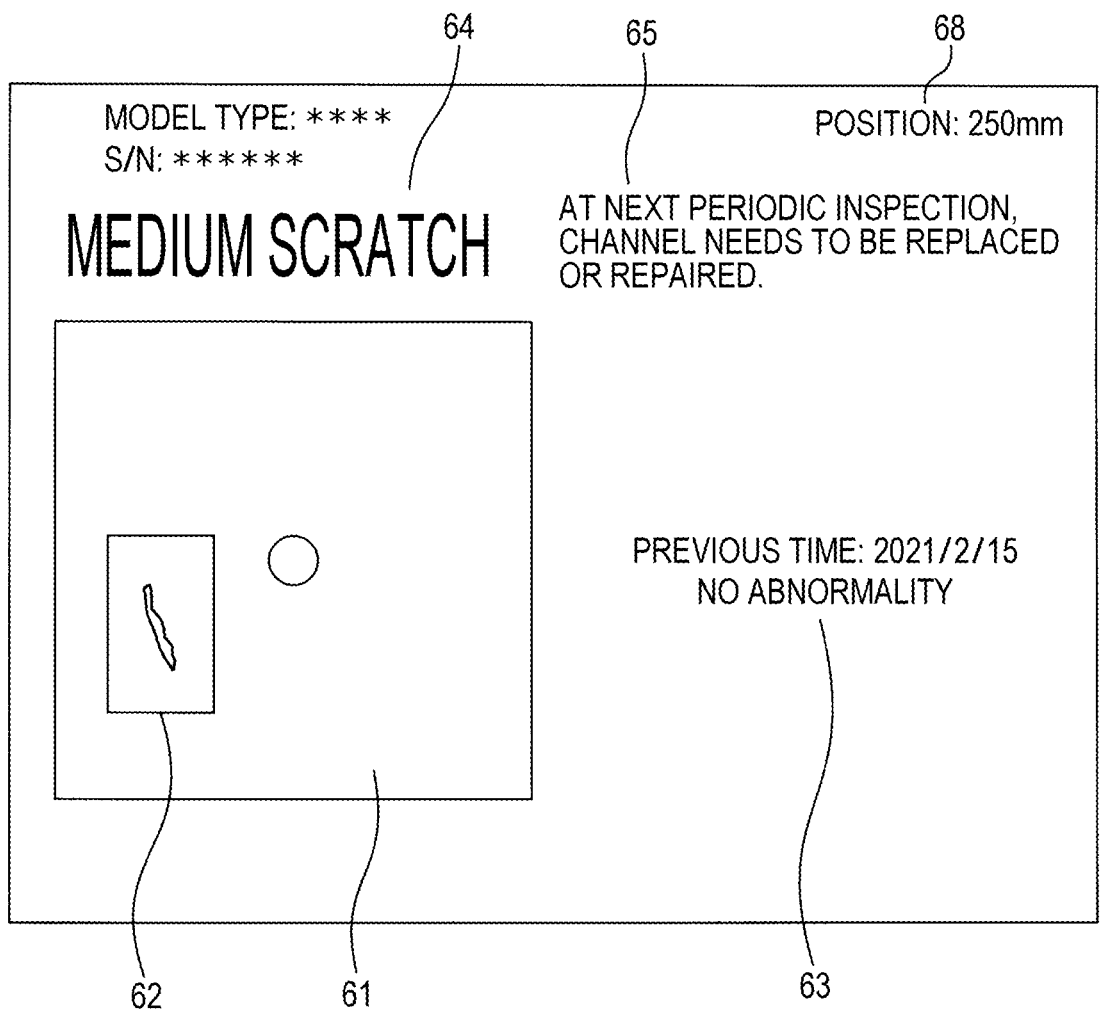
FIG. 11 is an explanatory diagram illustrating an exemplary screen according to the second embodiment.

FIGS. 10 and 11 are explanatory diagrams illustrating an example of a screen according to the second embodiment. FIG. 10 illustrates an example of a screen when it is determined that there is a "medium scratch." In addition to the inspection image field 61, the determination field 64, the notification contents field 65, the model type of the inspection target endoscope 40, and the like, a past information field 63 and a position field 68 are displayed on the screen.

The abnormal portion frame 62 indicating a portion where an abnormality has been detected is superimposed and displayed on the real-time inspection image displayed in the inspection image field 61. A message indicating that "medium scratch" is determined is displayed in the determination field 64. The notification contents corresponding to the determination result of "broken" is displayed in the notification contents field 65.

A position at which the real-time inspection image is captured is displayed in the position field 68. An inspection image captured in the past at the same position and the abnormal portion frame 62 are displayed in the past information field 63. Comparison description between the real-time inspection image and the inspection image captured in the past is displayed below the past information field 63. In the example illustrated in FIG. 10, a state of the detected scratch has not changed from the past state recorded in the inspection history DB 52.

FIG. 11 illustrates a display example when data corresponding to the position at which the abnormality has been found is not recorded in the inspection history DB 52. In the past information field 63, the previous inspection date and the fact that no abnormality is recorded at the position in the previous inspection are displayed.

According to the present embodiment, the user can easily confirm whether the found abnormality is an abnormality that has existed from the past or an abnormality that has been newly found. When the abnormality has existed from the past, the user can easily confirm whether the degree of abnormality has progressed as compared with the previous inspection.

Third Embodiment

The present embodiment illustrates an inspection system 10 that displays a report based on data recorded in an inspection history DB 52. Descriptions of portions common to those of the first embodiment will be omitted.

Figure 12:
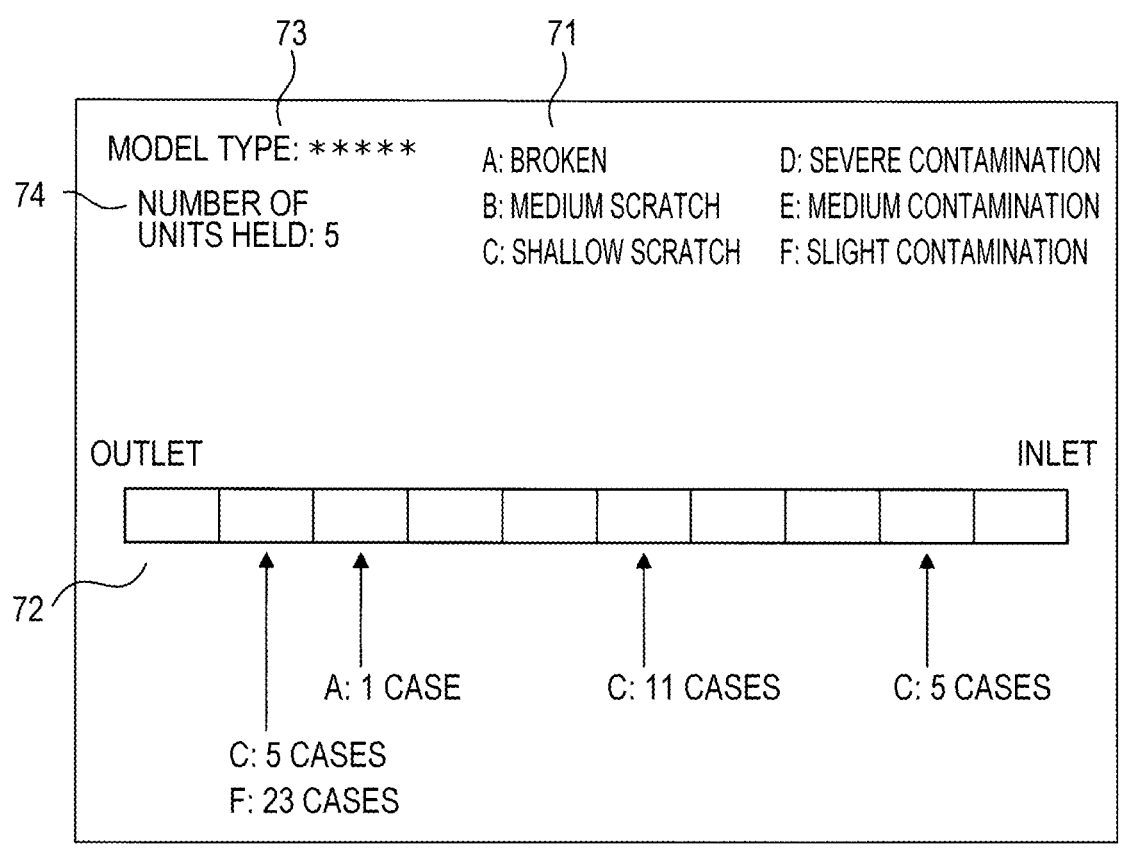
FIG. 12 is an explanatory diagram illustrating an exemplary screen for displaying a report.

FIG. 12 is an explanatory diagram illustrating an example of a screen for displaying a report. The report is generated based on the inspection history DB 52. For example, the control unit 21 generates a report and displays the report on the display unit 26. The control unit 21 may transmit the generated report to another computer or the like via the HIS. Another information processing device that can access the inspection history DB 52 may display the report screen. The report screen may be generated based on the inspection history DB 52 recorded by the plurality of inspection systems 10.

In an upper part of the screen illustrated in FIG. 12, a model field 73 indicating a model type of the inspection target endoscope 40, a number-of-units-held field 74 indicating the number of types of models held, and a legend field 71 are displayed. A history field 72 is displayed below the center of the screen illustrated in FIG. 12.

In the history field 72, the channel 45 equally divided into ten parts in the longitudinal direction is schematically displayed. The right side indicates the channel inlet 451 side, and the left side indicates the channel outlet 452 side. How many abnormalities such as "breakage" have been detected in the past in each of the regions divided into 10 equal parts is shown. For example, in a second region from the channel outlet 452 side, five "shallow scratches" and twenty-three "slight contaminations" are detected.

Since a process of generating the report illustrated in FIG. 12 based on the data recorded in the inspection history DB 52 can be performed through known data processing, the description thereof will be omitted.

The display of the history field 72 is exemplary. For example, a relationship between a position and the number of detections may be displayed with a bar graph, a line graph, or the like. Information regarding a case where the inspection target endoscope 40 is used in each endoscopic examination may be acquired from the HIS and, for example, a report may be generated in each procedure such as presence or absence of biopsy. The report may be generated for each doctor who has performed the endoscopic examination or for each co-medical staff who has performed the cleaning operation.

According to the present embodiment, it is possible to provide the inspection system 10 that generates a report in which information regarding a location or a procedure in which an abnormality is likely to occur in the inspection target endoscope 40 is summarized. The user using the report according to the present embodiment can examine a measure for preventing damage of the inspection target endoscope 40.

The report may be provided to a manufacturer of the inspection target endoscope 40. The manufacturer can use the report to develop the inspection target endoscope 40 that is hardly damaged.

Fourth Embodiment

The present embodiment relates to an inspection system 10 embedded in an endoscope cleaning and disinfecting device. Descriptions of portions common to those of the second embodiment will be omitted. The endoscope cleaning and disinfecting device is a device that automatically cleans and disinfects an endoscope. Since an endoscope cleaning and disinfecting device is known, a detailed description thereof will be omitted.

In the present embodiment, the inspection endoscope 30 and the advance and retreat device 39 are attached to a cleaning tank of an endoscope cleaning and disinfecting device. The inspection endoscope 30 and the advance and retreat device 39 may be cleaned and disinfected simultaneously with the inspection target endoscope 40. In this way, it is possible to prevent the inspection target endoscope 40 from being contaminated by the inspection endoscope 30.

The information processing device 20 also serves as a control unit of the endoscope cleaning and disinfecting device. That is, the control unit 21 according to the present embodiment has a function of a cleaning device control unit that controls the endoscope cleaning and disinfecting device.

After the endoscopic examination ends, a person in charge such as a nurse or an endoscopic technician performs bedside cleaning and manual cleaning of the inspection target endoscope 40. The person in charge sets the inspection target endoscope 40 in the endoscope cleaning and disinfecting device. The control unit 21 controls the endoscope cleaning and disinfecting device such that the inspection target endoscope 40 is cleaned and disinfected.

After the cleaning and disinfection ends, the control unit 21 inserts the insertion portion 31 into the channel 45 to perform inspection. When there is slight contamination to the extent of being removed by performing cleaning and disinfecting again, the control unit 21 controls the endoscope cleaning and disinfecting device such that the cleaning and disinfecting are performed again.

A camera that images the vicinity of the channel outlet 452 of the set inspection target endoscope 40 may be installed in the cleaning tank. Based on an image captured by the camera, the control unit 21 can detect that the insertion portion 31 has reached the channel outlet 452. By using a camera capable of capturing a high-resolution image as compared with the inspection endoscope 30, it is possible to provide the inspection system 10 capable of accurately determining a cleaning state of, for example, an observation optical system, an illumination optical system, an elevator, and the like in addition to the state of the channel 45.

Figure 13:
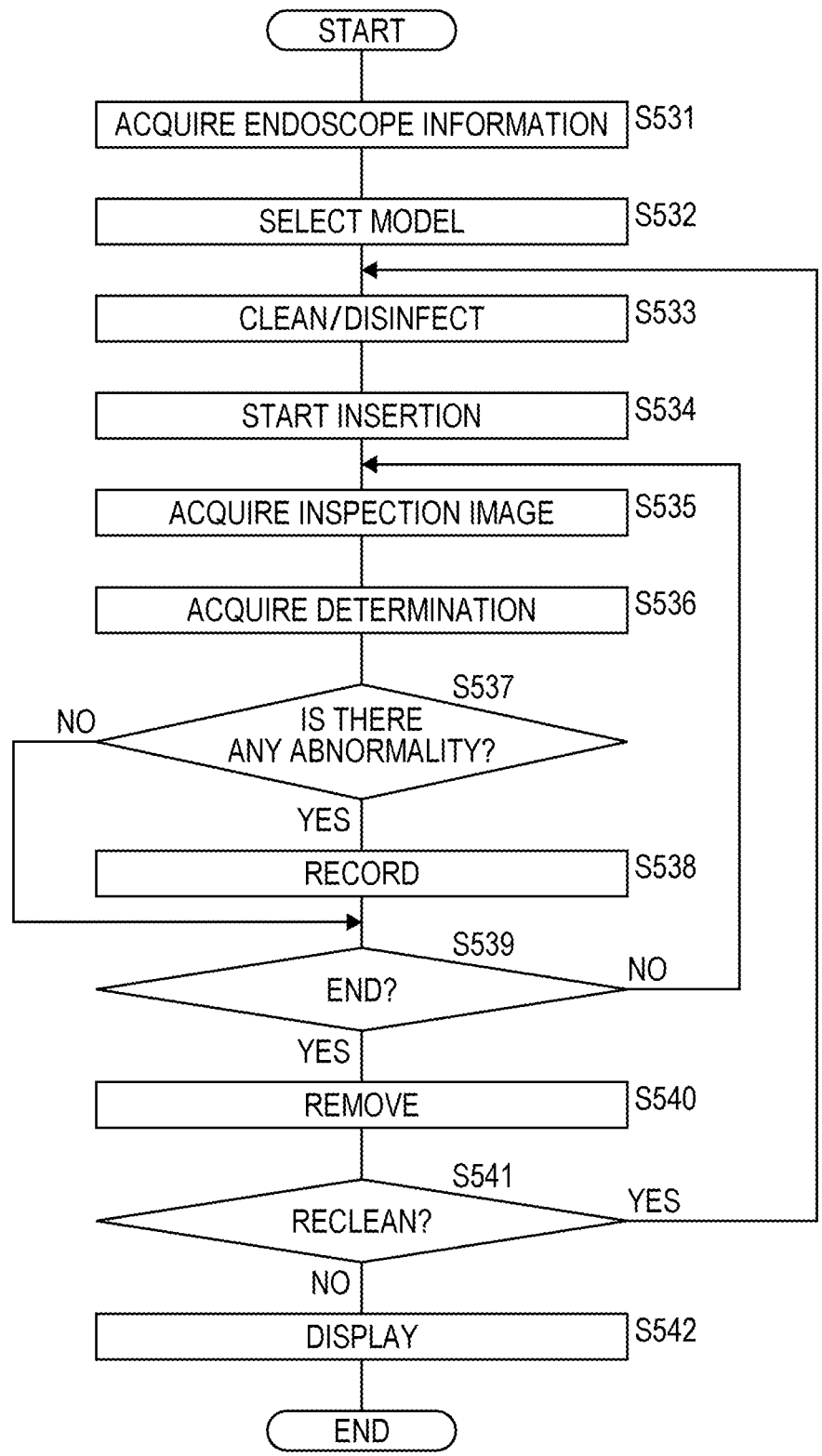
FIG. 13 is a flowchart illustrating a flow of processing of a program according to a fourth embodiment.

FIG. 13 is a flowchart illustrating a flow of processing of a program according to the fourth embodiment. The control unit 21 acquires information regarding the model type or the like of the inspection target endoscope 40 (step S531). The control unit 21 selects the model 51 corresponding to the model type of the inspection target endoscope 40 (step S532).

The control unit 21 causes the endoscope cleaning and disinfecting device to clean and disinfect the inspection target endoscope 40 (step S533). The control unit 21 controls the advance and retreat device 39 such that insertion of the insertion portion 31 into the channel 45 is started (step S534).

The control unit 21 acquires the inspection image transmitted from the inspection endoscope 30 (step S535). The control unit 21 inputs the inspection image acquired in step S535 to the model 51 selected in step S532 and acquires the output determination result (step S536).

The control unit 21 determines whether the determination result acquired from the model 51 includes information indicating an abnormality of the channel 45 (step S537). When it is determined that the information indicating the abnormality is included (YES in step S537), the control unit 21 generates a new record in the inspection history DB 52 and records a position, a determination result, and an inspection image when the inspection image determined to have the abnormality is captured (step S538).

When it is determined that information indicating abnormality is not included (NO in step S537) or after step S538 ends, the control unit 21 determines whether the inspection of the channel 45 ends (step S539). When it is determined that the inspection does not end (NO in step S539), the control unit 21 returns to step S535.

When it is determined that the inspection ends (YES in step S539), the control unit 21 controls the advance and retreat device 39 such that the insertion portion 31 is removed from the channel 45 (step S540). The control unit 21 determines whether to perform the recleaning based on the determination result recorded in the inspection history DB 52 in step S538.

For example, when a determination result such as "slight contamination" in which recleaning is necessary is included and a determination result such as "broken" in which the inspection target endoscope 40 cannot be used any more is not included, the control unit 21 determines to perform recleaning. When the recleaning has already been repeated a predetermined number of times, the control unit 21 determines that the recleaning is not performed.

When it is determined that the recleaning is performed (YES in step S541), the control unit 21 returns to step S533. When it is determined that the recleaning is not performed (NO in step S541), the control unit 21 displays the reprocessing result on the display unit 26 also serving as an operation panel of the endoscope disinfection and cleaning device (step S542). After that, the control unit 21 ends the processing.

Figure 14:
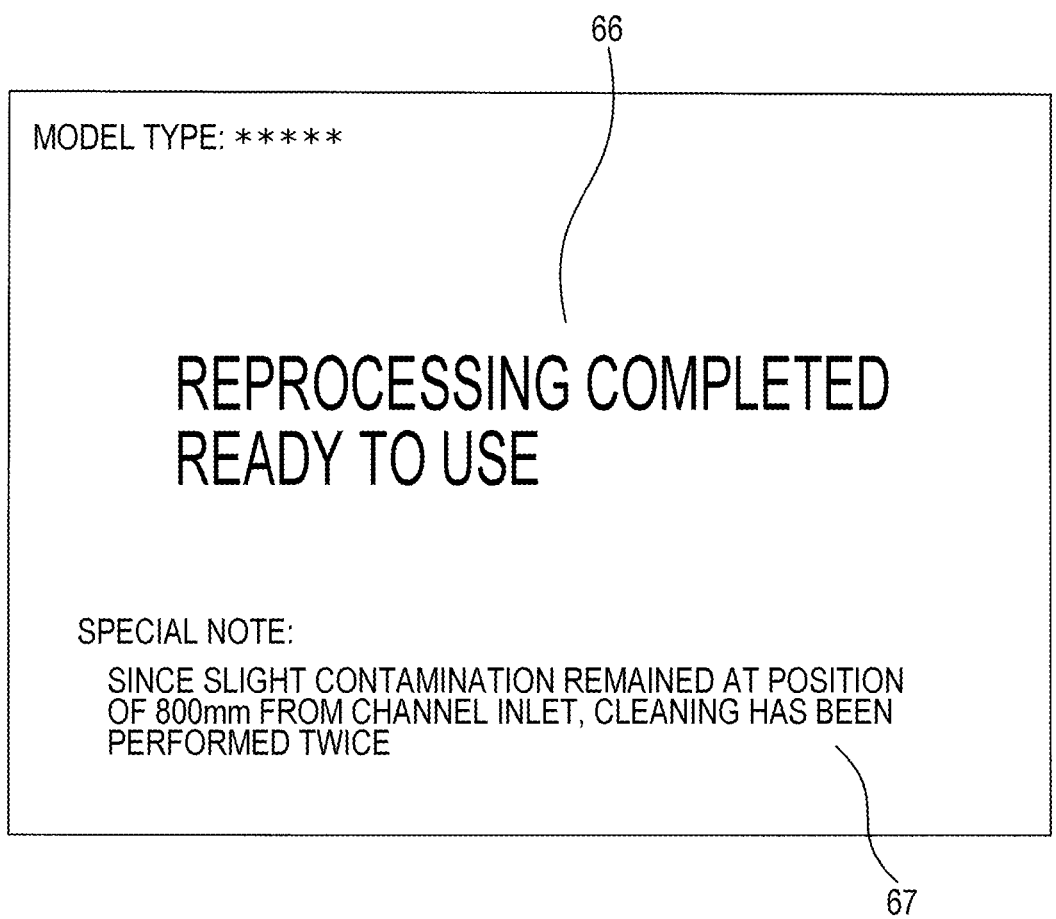
FIG. 14 is an explanatory diagram illustrating an exemplary screen according to the fourth embodiment.

FIG. 14 is an explanatory diagram illustrating an exemplary screen according to the fourth embodiment. FIG. 14 illustrates an exemplary screen displayed by the control unit 21 in step S542. A result field 66 indicating a result of the reprocessing is displayed at the center of the screen. A special note field 67 is displayed at the bottom of the screen.

In the example shown in FIG. 14, in step S541 of the first time, the control unit 21 determines that the recleaning associated with "slight contamination" is necessary (YES in step S541) and performs the second cleaning. Since "slight contamination" is not detected in step S541 of the second time, the control unit 21 displays the screen illustrated in FIG. 14 (step S542) and ends the processing.

A person in charge takes out the inspection target endoscope 40 from the endoscope cleaning and disinfecting device after the person confirms the screen illustrated in FIG. 14. When the fact that the inspection target endoscope 40 cannot be used due to "broken" or the like is displayed, the person in charge takes out the inspection target endoscope 40 and arranges a repair.

According to the present embodiment, it is possible to provide the endoscope cleaning and disinfecting device that performs cleaning and disinfection in accordance with the inspection target endoscope 40 with a small degree of contamination and automatically repeats cleaning as necessary. It is possible to provide the endoscope cleaning and disinfecting device and the inspection system 10 that reduce a damage caused due to a disinfectant solution or the like to the inspection target endoscope 40.

When it is determined that the recleaning is performed (YES in step S541), the control unit 21 may notify the person in charge that the manual cleaning needs to be performed again. For example, the control unit 21 notifies that it is necessary to perform the manual cleaning again when "medium contamination" remains, and automatically repeats the cleaning when only "slight contamination" remains.

The model 51 may be learned to output whether the degree of contamination is the degree of contamination that can be removed through the recleaning by the endoscope cleaning and disinfecting device or the degree of contamination that requires manual cleaning.

Fifth Embodiment

Figure 15:
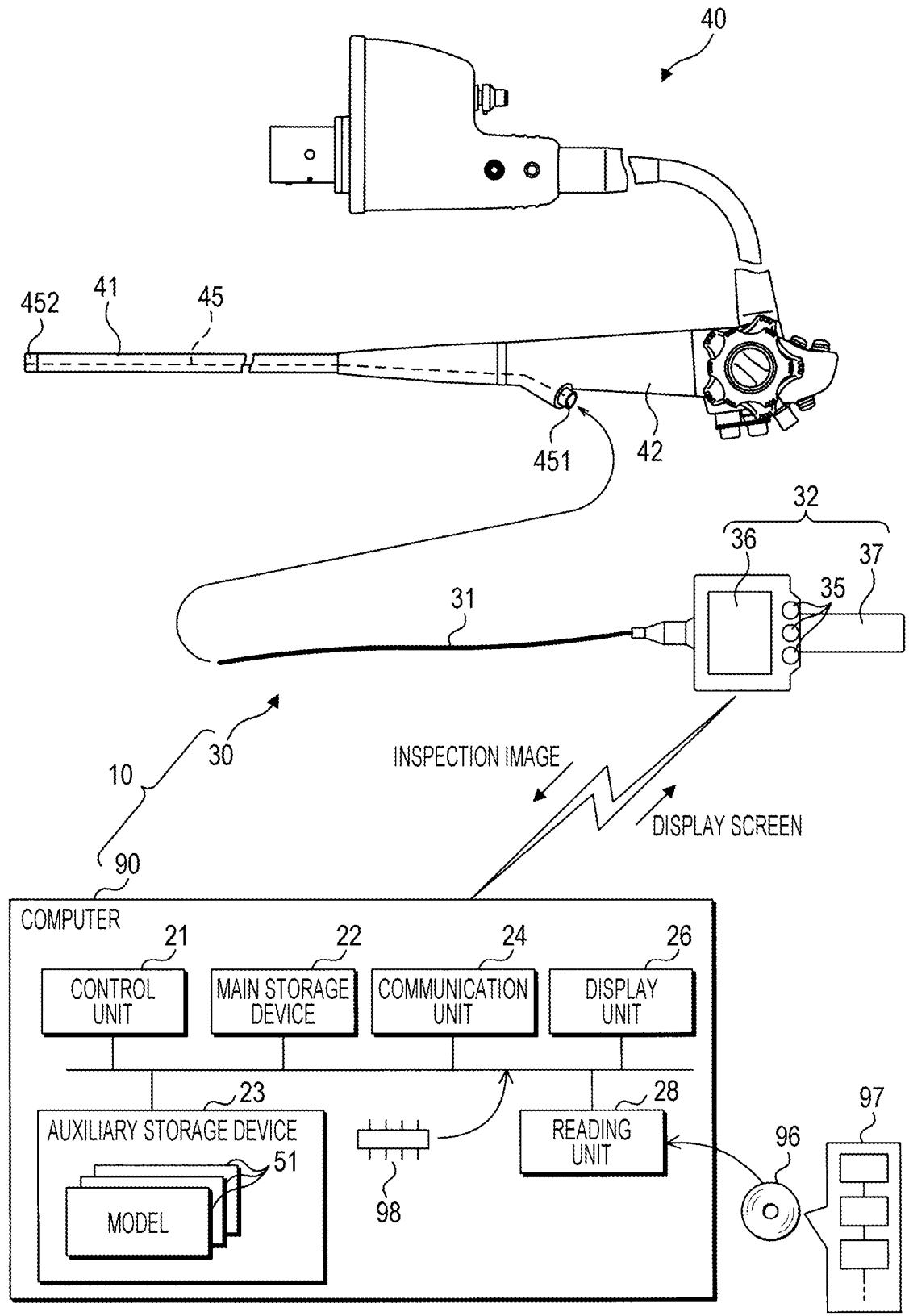
FIG. 15 is an explanatory diagram illustrating a configuration of an inspection system according to a fifth embodiment.

The present embodiment relates to a mode for implementing the inspection system 10 according to the present embodiment by operating a general-purpose computer 90 and a program 97 in combination. FIG. 15 is an explanatory diagram illustrating a configuration of the inspection system 10 according to the fifth embodiment. Descriptions of portions common to those of the first embodiment will be omitted.

The inspection system 10 according to the present embodiment includes the computer 90. The computer 90 includes the control unit 21, the main storage device 22, the auxiliary storage device 23, the communication unit 24, the display unit 26, a reading unit 28, and a bus. The computer 90 is an information device such as a general-purpose personal computer, a tablet, or a server computer.

The program 97 is recorded on a portable recording medium 96. The control unit 21 reads the program 97 via the reading unit 28 and stores the program in the auxiliary storage device 23. The control unit 21 may read the program 97 stored in a semiconductor memory 98 such as a flash memory mounted in the computer 90. The control unit 21 may download the program 97 from another server computer (not illustrated) connected via the communication unit 24 and a network (not illustrated) and may store the program 97 in the auxiliary storage device 23.

The program 97 is installed as a control program of the computer 90 and is loaded and executed on the main storage device 22. Accordingly, the computer 90 functions as the above-described information processing device 20.

Sixth Embodiment

Figure 16:
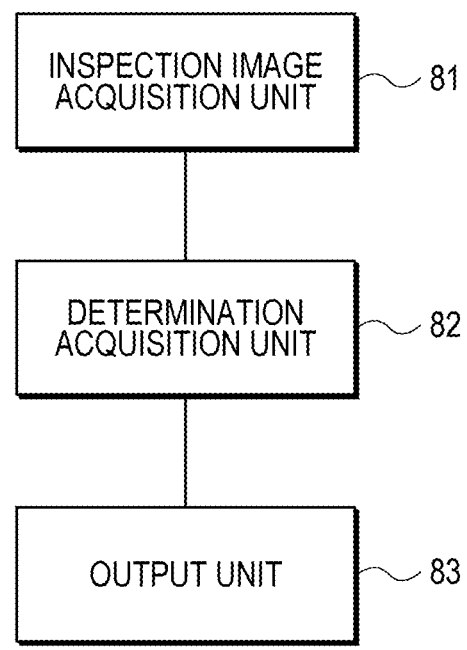
FIG. 16 is a functional block diagram of an information processing device according to a sixth embodiment.

FIG. 16 is a functional block diagram of the information processing device 20 according to the sixth embodiment. The information processing device 20 includes an inspection image acquisition unit 81 that acquires an inspection image captured by the inspection endoscope 30 inserted into the channel 45 of the inspection target endoscope 40; a determination acquisition unit 82 that inputs the inspection image acquired by the inspection image acquisition unit 81 to the model 51 that outputs a determination prediction regarding the state of the channel 45 when the inspection image is input, and acquires the determination prediction to be output; and an output unit 83 that outputs the inspection image and the determination prediction in association.

The technical features (constituent elements) described in the embodiments can be combined with each other to form novel technical features in combination.

It should be considered that the embodiments disclosed herein are exemplary in all respects and are not limited. The scope of the present invention is defined not by the foregoing meanings but by the claims and is intended to include meanings equivalent to the claims and all modifications within the scope.

REFERENCE SIGNS LIST

10 Inspection system
20 Information processing device
21 Control unit
22 Main storage device
23 Auxiliary storage device
24 Communication unit
26 Display unit
28 Reading unit
30 Inspection endoscope
31 insertion portion
32 operation unit
35 Operation button
36 Display unit
37 Grip portion
39 Advance and retreat device
40 Inspection target endoscope
41 insertion portion
42 operation unit
45 Channel
451 Channel inlet
452 Channel outlet
51 Model
52 Inspection history DB
61 Inspection image field
62 Abnormal portion frame
63 Past information field
64 Determination field
65 Notification contents field
66 Result field
67 Special description field
68 Position field
71 Legend field
72 History field
73 Model type field
74 Number-of-units-held field
81 Inspection image acquisition unit
82 Determination acquisition unit
83 Output unit
90 Computer
96 Portable recording medium
97 Program
98 Semiconductor memory

The invention claimed is:

1. An information processing device comprising:
a processor; and
a memory including at least one set of instructions, which when executed by the processor, causes the processor to operate as:
an inspection image acquisition processor configured to acquire an inspection image captured by an inspection endoscope inserted into a channel of an inspection target endoscope;
a determination acquisition processor configured to input the inspection image acquired by the inspection image acquisition processor to a model that outputs a determination prediction regarding a state of the channel when the inspection image is input, and to acquire the determination prediction to be output;
a position acquisition processor configured to acquire a position at which the inspection image is captured;
an output configured to output the inspection image and the determination prediction, and the position acquired by the position acquisition processor in association;
an inspection history recording processor configured to record the inspection image, the determination prediction, and the position acquired by the position acquisition processor in association; and
an extraction processor configured to extract a past determination prediction corresponding to the position acquired by the position acquisition processor, from a record recorded by the inspection history recording processor, wherein:
the determination prediction acquired by the determination acquisition processor and the past determination prediction extracted by the extraction processor are output in association.

2. The information processing device according to claim 1, wherein
the position is a length from an inlet of the channel.

3. The information processing device according to claim 1, wherein
the determination prediction includes a prediction regarding whether or not repair is needed and prediction regarding whether or not cleaning is needed.

4. The information processing device according to claim 1, wherein the least one set of instructions, when executed by the processor, further causes the processor to operate as:
an advance and retreat control processor configured to control an advance and retreat actuator that advances and retreats an insertion portion of the inspection endoscope inserted into the channel.

5. An information processing device comprising:
a processor; and
a memory including at least one set of instructions, which when executed by the processor, causes the processor to operate as:
an inspection image acquisition processor configured to acquire an inspection image captured by an inspection endoscope inserted into a channel of an inspection target endoscope;
a determination acquisition processor configured to input the inspection image acquired by the inspection image acquisition processor to a model that outputs a determination prediction regarding a state of the channel when the inspection image is input, and to acquire the determination prediction to be output;
an output configured to output the inspection image and the determination prediction in association;
an endoscope information acquisition processor configured to acquire endoscope information regarding an inspection target endoscope; and
a model selection processor configured to select a model corresponding to the endoscope information from a plurality of models.

6. The information processing device according to claim 5, wherein
the model exists for each application of the inspection target endoscope.

7. The information processing device according to claim 5, wherein
the model exists for each inner diameter of the channel.

8. An inspection system comprising:
an inspection endoscope comprising:
- an image sensor configured to be inserted into a channel of an inspection target endoscope and capture an inspection image; and
- an inspection image output configured to output the inspection image, and
an information processing device comprising:
a processor; and
a memory including at least one set of instructions, which when executed by the processor, causes the processor to operate as:
- an inspection image acquisition processor configured to acquire the inspection image output from the inspection image output; and
- a determination acquisition processor configured to input the inspection image acquired by the inspection image acquisition processor to a model that outputs a determination prediction regarding a state of the channel when the inspection image is input, and to acquire the output determination prediction;
- an output configured to output the inspection image and the determination prediction in association; and
- a cleaning control processor configured to control a cleaner that cleans the inspection target endoscope, wherein when the determination prediction indicates that it is necessary to reclean the inspection target endoscope, cleaning control processor causes the cleaner to reclean the inspection target endoscope.

9. The inspection system according to claim 8 further comprising
an advance and retreat actuator configured to advance and retreat an insertion portion of the inspection endoscope inserted into the channel.

10. The inspection system according to claim 8, wherein the inspection endoscope is cleaned by the cleaner along with the inspection target endoscope.

* * * * *